United States Patent [19]
Fabiano et al.

[11] Patent Number: 6,063,792
[45] Date of Patent: May 16, 2000

[54] METHODS AND COMPOSITIONS FOR TREATING URINARY INCONTINENCE USING ENANTIOMERICALLY ENRICHED (S)-TRIHEXYPHENIDYL

[75] Inventors: Vincent L. Fabiano, Princeton, N.J.; John R. McCullough, Hudson, Mass.

[73] Assignee: Sepracor Inc., Marlborough, Mass.

[21] Appl. No.: 09/214,170

[22] PCT Filed: Jun. 27, 1997

[86] PCT No.: PCT/US97/11643

§ 371 Date: Dec. 29, 1998

§ 102(e) Date: Dec. 29, 1998

[87] PCT Pub. No.: WO98/00141

PCT Pub. Date: Jan. 8, 1998

Related U.S. Application Data

[60] Provisional application No. 60/020,733, Jul. 1, 1996.

[51] Int. Cl.$^7$ .................................................. A01N 43/40
[52] U.S. Cl. ........................... 514/315; 514/878; 514/906
[58] Field of Search ................................... 514/315, 878, 514/906

[56] References Cited

U.S. PATENT DOCUMENTS 4,945,097  7/1990  Olney ...................................... 514/318

OTHER PUBLICATIONS

Chemical Abstract 121:292670, "Antagonism by (R)–and (S)–trihexyphenidyl of Muscarinic Stimulation of Adenyl Cyclase . . . ", Mar. 1994.

Chemical Abstract 89:99555g, "The Fate of Prindol in the Organism: Pharmacokinetics and Distribution in Animals", Apr. 1978.

Poyurovsky, M. et al., "Trihexyphenidyl as a possible therapeutic option in clozapine–induced nocturnal ensuresis," *Int'l Clin Psychopharm*, 11:61–63 (1996).

Foote, J. et al., "Neurogenic Dysfunction of the Urinary Bladder in Parkinson's Disease," *Primary Care* 4:463–473 (1977).

Waelbrocck, M. et al., "Stereoselective interaction of procyclidine, hexahydro–difenidol, hexbutinol and oxyphencyclimine, and of related antagonists, with four muscarinic receptors," *European Journal of Pharmacology —Molecular Pharmacology Section,* 227:33–42 (1992).

Armstrong, D. et al., "Separation of Drug Stereoisomers by the Formation of β–Cyclodextrin Complexes," *Science,* 232:1132–1135 (1986).

*Primary Examiner*—Frederick Krass
*Attorney, Agent, or Firm*—Heslin & Rothenberg, P.C.

[57] ABSTRACT

Disclosed are methods for treating urinary incontinence using enantiomerically enriched (S)-trihexyphenidyl.

18 Claims, No Drawings

6,063,792

METHODS AND COMPOSITIONS FOR TREATING URINARY INCONTINENCE USING ENANTIOMERICALLY ENRICHED (S)-TRIHEXYPHENIDYL

CROSS REFERENCE TO RELATED APPLICATIONS

This application is the United States National Phase of International Patent Application PCT/US97/11643, filed Jun. 27, 1997, and claims the priority of United States Provisional Patent Application Ser. No. 60/020,733, filed Jul. 1, 1996, the entire contents of each is hereby incorporated by reference.

FIELD OF THE INVENTION

The present invention relates to methods for treating urinary incontinence, such as incontinence caused by bladder detrusor muscle instability, and to pharmaceutical compositions for such treatment.

BACKGROUND OF THE INVENTION

Urinary incontinence is a prevalent problem that affects people of all ages and levels of physical health, both in healthcare settings and in the community at large. At present, urinary incontinence afflicts 15–30% of elderly people living at home, one-third of those living in acute-care settings, and at least one-half of those in long-term care institutions (R. M. Resnick, *Lancet* 346:94 (1995)). Medically, it predisposes persons to urinary tract infections, pressure ulcers, perineal rashes, and urosepsis. Psychosocially, urinary incontinence is associated with embarrassment, social stigmatization, depression, and with the risk of institutionalization (Herzo et al., *Annu. Rev. Gerontol. Geriatr.,* 9:74 (1989)). Economically, the costs are great; in the United States alone, over $10 billion is spent per annum managing incontinence.

Treatments for incontinence include drugs with bladder relaxant properties, i.e., which help to control bladder detrusor muscle overactivity. Such drugs are effective in 80 to 85% of patients with uninhibited bladder contractions, with anticholinergic medications representing the mainstay of this type of treatment. For example, anticholinergics such as propantheline bromide, and combination smooth muscle relaxant/anticholinergics such as racemic oxybutynin and dicyclomine, have been used to treat urge incontinence. (See, e.g., A. J. Wein, *Urol. Clin. N. Am.,* 22:557–77 (1995).)

No treatment for incontinence, including existing drug therapies, has achieved complete success with all classes of incontinent patients, and without significant side effects. For example, adverse effects, such as drowsiness, dry mouth, constipation, blurred vision, headaches, and cardiac arrhythmia which are related to the anticholinergic activity of drugs such as racemic oxybutynin, occur frequently and can be sufficiently troublesome to necessitate discontinuing treatment in up to 25% of patients, depending on the dosage. Yet, despite the occurrence of unwanted anticholinergic effects in many patients, and an apparent lack of efficacy in the elderly institutionalized population, racemic oxybutynin nevertheless is considered the drug of first choice in patients with bladder detrusor muscle hyperactivity when pharmacological therapy is indicated (cf. Yarllur et al., *Drugs Aging,* 6:243 (1995)).

Trihexyphenidyl, 3-(1-piperidyl)-1-cyclohexyl-1-propanol, a synthetic antispasmotic drug, is described as being useful in treating parkinsonism, and has been used in muscarinic receptor binding studies (Lambrecht et al., *Eur. J. Pharmacol.,* 155:167–170 (1988); Waelbroeck et al., *Brit. J. Pharmacol.,* 109:360–370 (1993)). Similar adverse effects to those for anticholinergic drugs may result with the use of trihexyphenidyl (cf.*Physician's Desk Reference,* 50th Edition, page 1368 (1996)).

SUMMARY OF THE INVENTION

The present invention provides methods and compositions for treatment of urinary incontinence, including, e.g., bladder detrusor muscle instability incontinence, stress incontinence, urge incontinence, overflow incontinence, enuresis, and post-prostectomy incontinence, with (S)-trihexyphenidyl. The methods of the present invention provide for treatment of incontinence with fewer adverse effects than occur upon administration of racemic trihexyphenidyl.

One aspect of the present invention relates to methods for treating urinary incontinence by administration to a subject in need thereof a therapeutically effective amount of enantiomerically enriched (S)-trihexyphenidyl, or a pharmaceutically acceptable salt thereof. In a preferred embodiment of this method, the enantiomerically enriched (S)-trihexyphenidyl, or a pharmaceutically acceptable salt thereof, is substantially free of (R)-trihexyphenidyl.

The present invention also relates to methods for treating bladder detrusor muscle instability comprising administration to a subject in need thereof a therapeutically effective amount of enantiomerically enriched (S)-trihexyphenidyl, or a pharmaceutically acceptable salt thereof. Preferably, the enantiomerically enriched (S)-trihexyphenidyl, or a pharmaceutically acceptable salt thereof, is substantially free of (R)-trihexyphenidyl.

Another aspect of the present invention relates to pharmaceutical compositions for the treatment of urinary incontinence comprising enantiomerically enriched (S)-trihexyphenidyl, or a pharmaceutically acceptable salt thereof, and a pharmaceutically acceptable carrier. In a preferred embodiment, the pharmaceutical compositions of the present invention comprise (S)-trihexyphenidyl, or a pharmaceutically acceptable salt thereof, substantially free of (R)-trihexyphenidyl.

The present invention also provides for formulating the pharmaceutical compositions of the present invention, comprising enantiomerically enriched (S)-trihexyphenidyl, or a pharmaceutically acceptable salt thereof, and a pharmaceutically acceptable carrier, in pharmaceutical unit dosage forms, including, e.g., tablets and soft elastic gelatin capsules.

Yet another embodiment of the present invention relates to a kit for treating urinary incontinence, such as bladder detrusor muscle instability incontinence, stress incontinence, urge incontinence, overflow incontinence, enuresis, and post-prostectomy incontinence, wherein said kit comprises a pharmaceutical composition comprising enantiomerically enriched (S)-trihexyphenidyl, or a pharmaceutically acceptable salt thereof, and a pharmaceutically acceptable carrier, and instructions for administering the same while reducing or eliminating anticholinergic adverse effects associated with administration of racemic trihexyphenidyl, or other incontinence drugs with anticholinergic action. Preferably, the enantiomerically enriched (S)-trihexyphenidyl, or a pharmaceutically acceptable salt thereof, is substantially free of (R)-trihexyphenidyl.

DETAILED DESCRIPTION OF THE INVENTION

It is known that urinary incontinence can be caused by uncontrolled or unstable bladder contractions, particularly of the bladder detrusor muscle which serves to force fluids out of the bladder. The major proportion of the neurohumeral stimulus for physiologic bladder contraction is acetylcholine-induced stimulation of postganglionic muscarinic receptor sites on bladder smooth muscle. Consistent with this observation, most pharmacologic treatments for incontinence associated with uninhibited bladder contractions include medications with anticholinergic and smooth muscle relaxant properties. However, as set out above, many of the anticholinergic agents which have been used for the treatment of incontinence often have adverse effects associated with their anticholinergic actions, which result in at least periodic discontinuation of use in a significant portion of the treated population.

The present invention relates to compositions and methods for the treatment of bladder instability in mammals, such as humans. More specifically, this invention provides enantiomerically enriched preparations of (S)-trihexyphenidyl and methods for their use in the treatment of urinary incontinence, including, e.g., bladder detrusor muscle instability incontinence, stress incontinence, urge incontinence, overflow incontinence, enuresis, and post-prostectomy incontinence. One feature of the subject non-racemic preparations of (S)-trihexyphenidyl derives from the enantiomer's pharmacological advantage over the racemate in terms of its principal therapeutic and side effect profile. Certain deleterious local and/or systemic adverse effects of the racemic mixture, e.g., drowsiness, xerostomia, mydriasis, constipation, cycloplegia, cardiac arrhythmia and/or epistaxis may be reduced through treatment with enantiomerically enriched (S)-trihexyphenidyl.

The chemical structure of (S)-trihexyphenidyl is as set forth in Formula I:

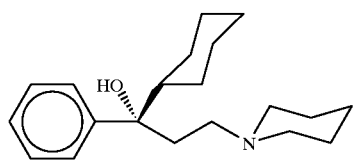

I

In one aspect, the present invention provides a method for treating urinary incontinence using (S)-trihexyphenidyl, which results in a reduction of the adverse effects associated with administration of racemic trihexyphenidyl. The method comprises administering to a patient in need thereof a pharmaceutically effective amount of (S)-trihexyphenidyl, or a pharmaceutically acceptable salt thereof, substantially free of (R)-trihexyphenidyl. In a preferred embodiment, the methods of the present invention are used to treat urinary incontinence due to bladder detrusor muscle instability. Such instability may result in, for example, stress incontinence or urge incontinence, or combination thereof, and/or enuresis.

In another aspect, the present invention provides pharmaceutical compositions which comprise an enantiomerically enriched preparation of (S)-trihexyphenidyl, or a pharmaceutically acceptable salt thereof, formulated together with one or more pharmaceutically acceptable carriers (additives) and/or diluents. As described in detail below, the pharmaceutical compositions of the present invention may be specially formulated for administration in solid or liquid form, including those adapted for oral administration, parenteral administration, or topical application.

For convenience, certain terms employed in the specification, examples, and appended claims are collected here.

The term "chiral" refers to molecules which have the property of non-superimposability of the mirror image partner, while the term "achiral" refers to molecules which are superimposable on their mirror image partner. With respect to the nomenclature of a chiral center, the terms "S" and "R" configuration are as defined by the IUPAC 1974 Recommendations for Section E., Fundamental Stereochemistry, *Pure Appl. Chem.*, 45:13–30 (1976). The terms racemate and enantiomer will be used in their normal context to describe the stereochemistry of trihexyphenidyl preparations.

The terms "enantiomerically enriched" and "non-racemic", as used interchangeably herein with reference to preparations of trihexyphenidyl, refer to trihexyphenidyl compositions in which the (S)-trihexyphenidyl enantiomer is enriched, compared to a control mixture of (S)-trihexyphenidyl and (R)-trihexyphenidyl enantiomers. Unless otherwise specified, such terms refer to trihexyphenidyl compositions in which the ratio of (S)-trihexyphenidyl to (R)-trihexyphenidyl enantiomers is greater than 1:1 by weight. For instance, an enantiomerically enriched preparation of (S)-trihexyphenidyl, means a preparation of trihexyphenidyl having greater than 50% by weight of the (S)-trihexyphenidyl enantiomer relative to the (R)-trihexyphenidyl enantiomer, more preferably at least 75% by weight, and even more preferably at least 80% by weight. Of course, the enrichment can be much greater than 80% by weight, providing a "substantially enantiomerically enriched" or a "substantially non-racemic" preparation, which refers to preparations of trihexyphenidyl which have at least 85% by weight of the (S)-trihexyphenidyl enantiomer relative to the (R)-trihexyphenidyl enantiomer, more preferably at least 90% by weight, and even more preferably at least 95% by weight. The term "substantially free of (R)-trihexyphenidyl" will be understood to have similar purity ranges., i.e., at least 85% by weight of the (S)-trihexyphenidyl enantiomer relative to the (R)-trihexyphenidyl enantiomer, more preferably at least 90% by weight, and even more preferably at least 95% by weight.

The term "adverse effects" as used herein, refers to effects associated with administration of racemic trihexyphenidyl, which are not part of the desired therapeutic effect of the drug. With respect to the treatment of urinary incontinence, such adverse effects, include, for illustrative purposes, drowsiness, epistaxis, xerostomia, mydriasis, cycloplegia, unstable cardiovascular status such as arrhythmia (e.g., tachycardia or palpitations), increased ocular pressure, nausea, constipation, decreased sweating, impotence, and/or dermal manifestations such as urticaria.

The term "epistaxis" refers to nosebleeds, e.g., hemorrhage from the nose. Epistaxis is a side effect of anticholinergics in children.

The term "xerostomia" refers to dryness of the mouth due to lack of normal secretion.

The term "mydriasis" refers to dilation of the pupil, and often results in blurred vision.

The term "cycloplegia" refers to paralysis of the ciliary muscle; paralysis of accommodation.

The term "enuresis" refers to the involuntary discharge of urine, and "nocturnal enuresis" refers to involuntary discharge of urine during sleep at night.

Separation of enantiomers can be accomplished in several ways known in the art. (See, e.g., Hermanssen et al., *J. Chromat.*, 694:57–69 (1995)). For example, a racemic mixture of two enantiomers can be separated by chromatography using a chiral stationary phase (see, e.g., "Chiral Liquid Chromatography", W. J. Lough, Ed. Chapman and Hall, New York (1989)). Enantiomers can also be separated by classical resolution techniques. For example, formation of diastereometric salts and fractional crystallization can be used to separate enantiomers. For the separation of enantiomers of carboxylic acids, the diastereometric salts can be formed by addition of enantiomerically pure chiral bases such as brucine, quinine, ephedrine, strychnine, and the like. Alternatively, diastereometric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

In addition to separation techniques such as those described above, the active enantiomer of trihexyphenidyl can be synthesized by stereospecific synthesis to produce only the desired optical isomer using methodology well known to those skilled in the art. (See, e.g., Sjö et al., *Acta Chemica Scandinavia*, 47:1019–1024 (1993); Schjekderup et al., *Acta Chemica Scandinavia*, B41:356–361 (1987)). Chiral synthesis can result in products of high enantiomeric purity. However, in some cases, the enantiomeric purity of the product is not sufficiently high. The skilled artisan will appreciate that the separation methods described above can be used to further enhance the enantiomeric purity of trihexyphenidyl obtained by chiral synthesis.

The optical purity of the (S)-trihexyphenidyl can be determined by methods known in the art. For example, a sample of the trihexyphenidyl can be analyzed by high performance liquid chromatography on a chiral chromatographic column. Another method of determining optical purity involves making a chiral ester, such as a Mosher ester, of a trihexyphenidyl sample, and analyzing the NMR spectrum for the presence of the undesired enantiomer.

In preferred embodiments, (S)-trihexyphenidyl is substantially free of (R)-trihexyphenidyl. "Substantially free" as used herein, means that at least 85% by weight of the total trihexyphenidyl present is the (S)-trihexyphenidyl enantiomer; more preferably at least 90% by weight, and still more preferably at least 95% by weight is the (S)-trihexyphenidyl enantiomer. In a more preferred embodiment, at least 99% by weight of the total trihexyphenidyl present is the (S)-trihexyphenidyl enantiomer.

(S)-trihexyphenidyl can be used to treat urinary incontinence, including, e.g., bladder detrusor muscle instability incontinence, stress incontinence, urge incontinence, overflow incontinence, enuresis, and post-prostectomy incontinence, by administration to a patient according to any suitable route of administration. (See, *Remington:The Science and Practice of Pharmacy*, Nineteenth Edition, Chapters 83–95 (1995).) For example, a preferred method of administration is oral administration. Another preferred route of administration is intravenous administration. A particularly preferred route of administration is intravesical delivery, i.e., administration directly to the bladder, e.g., by injection or infusion.

According to the present invention, (S)-trihexyphenidyl is preferably administered as a pharmaceutical formulation (composition). The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As set out above, (S)-trihexyphenidyl contains a quaternary amino functional group, and thus is capable of forming pharmaceutically acceptable salts. The term "pharmaceutically acceptable salts" in this respect, refers to the relatively non-toxic, inorganic and organic salts of (S)-trihexyphenidyl. These salts can be prepared in situ during the final isolation and purification of the (S)-trihexyphenidyl. Representative salts include the bromide, chloride, hydrobromide, hydrochloride, sulfate, bisulfate, phosphate, nitrate, acetate, valerate, oleate, palmitate, stearate, laurate, benxoate, lactate, phosphate, tosylate, citrate, maleate, fumarate, succinate, tartrate, naphthylate, mesylate, glucoheptonate, lactobionate, and laurylsulfonate salts and the like. (See, e.g., Berge et al., "Pharmaceutical Salts", *J. Pharm. Sci.,* 66:1–19 (1977).)

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which is combined with a carrier material to produce a single dosage form will vary depending upon the host being treated, and the particular mode of administration. The amount of active ingredient which may be combined with a carrier material to produce a single dosage form preferably will be that amount of (S)-trihexyphenidyl which produces a therapeutic effect. Generally, the amount of the active ingredient will range from about 1% to about 99% of the total formulation, preferably from about 5% to about 70%, and most preferably from about 10% to about 30%.

Methods of preparing these formulations or compositions include the step of bringing into association (S)-trihexyphenidyl with a pharmaceutically acceptable carrier and, optionally, one or more accessory ingredients. In general, the formulations are prepared by uniformly and intimately bringing into association (S)-trihexyphenidyl with liquid carriers, or finely divided solid carriers, or both, and any optional accessory ingredients, and then, if necessary, shaping the product.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the (S)-trihexyphenidyl from one organ, or portion of the body, to another organ or portion of the body. Each carrier must be "acceptable" in the sense of being compatible with the other ingredients of the formulation and not injurious to the patient.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations (see, Remington: The Science and Practice of Pharmacy, Nineteenth Edition, Chapter 80 (1995).)

Formulations of the present invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as a gelatin and glycerin, or sucrose and acacia), or as soft elastic gelatin capsules, and/or as mouth washes and the like, each containing a predetermined amount of a compound of the present invention as an active ingredient. (S)-trihexyphenidyl may also be administered as a bolus, electuary or paste.

In solid dosage forms of the present invention for oral administration (capsules, tablets, pills, dragees, powders, granules and the like), the active ingredient is mixed with one or more pharmaceutically acceptable carriers, such as sodium citrate or dicalcium phosphate, and/or may also be mixed with one or more of any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Release agents, coating agents, sweetening, flavoring and perfuming agents, preservatives and antioxidants can also be present in the compositions of the present invention. Examples of pharmaceutically acceptable antioxidants include: (1) water soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), and/or surface-active or dispersing agents. Molded tablets may be made by molding in a suitable machine a mixture of the powdered (S)-trihexyphenidyl moistened with an inert, liquid diluent.

The pharmaceutical compositions of the present invention may also be formulated in a soft elastic gelatin capsule unit dosage form by using conventional methods, well-known in the art (see, e.g., Ebert, Pharm. Tech., 1(5):44–50(1977)). Soft elastic gelatin capsules have a soft, globular, gelatin shell somewhat thicker than that of hard gelatin capsules, wherein a gelatin is plasticized by the addition of glycerin, sorbitol, or a similar polyol. The hardness of the capsule shell may be changed by varying the type of gelatin and the amounts of plasticizer and water. The soft gelatin shells may contain a preservative to prevent the growth of fungi, such as methyl- and propylparabens and sorbic acid. The active ingredient may be dissolved or suspended in a liquid vehicle or carrier, such as vegetable or mineral oils, glycols such as polyethylene glycol and propylene glycol, triglycerides, surfactants such as polysorbates, or a combination thereof.

The tablets, and other dosage forms of the pharmaceutical compositions of the present invention, such as dragees, capsules, pills and granules, may optionally be scored or prepared with coatings and shells, such as enteric coatings and other coatings well known in the pharmaceutical formulating art.

The pharmaceutical compositions of the present invention may also be formulated so as to provide slow or controlled release of the active ingredient therein using, for example, hydroxypropylmethyl cellulose in varying proportions to provide the desired release profile, other polymer matrices, liposomes and/or microspheres. They may also be administered by controlled release means and delivery devices such as those in U.S. Pat. Nos. 3,845,770; 3,916,899; 3,536,809; 3,598,123; and 4,008,796; and PCT published application WO 92/20377.

The pharmaceutical compositions of the present invention may also optionally contain opacifying agents and may be formulated such that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of (S)-trihexyphenidyl include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions of the present invention can also include adjuvants such as wetting agents, emulsifying and suspending agents, sweetening, flavoring, coloring, perfuming and preservative agents.

Suspensions, in addition to the active (S)-trihexyphenidyl, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the present invention for rectal and vaginal administration may be presented as a suppository, which may be prepared by mixing one or more compounds of the invention with one or more suitable non-irritating excipients or carriers comprising, for example, cocoa butter, polyethylene glycol, a suppository wax or a salicylate. Such formulations of the present invention are solid at room temperature, but liquid at body temperature and, therefore, will melt in the rectum or vaginal cavity and release the active (S)-trihexyphenidyl.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of (S)-trihexyphenidyl include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Formulations of the present invention in the form of ointments, pastes, creams and gels may contain, in addition to (S)-trihexyphenidyl, excipients, such as animal and vegetable fats, oils, waxes, paraffins, starch, tragacanth, cellulose derivatives, polyethylene glycols, silicones, bentonites, silicic acid, talc and/or zinc oxide, or mixtures thereof.

Powders and sprays may contain, in addition to (S)-trihexyphenidyl, excipients such as lactose, talc, silicic acid, aluminum hydroxide, calcium silicates and polyamide powder, or mixtures of these substances. Sprays may additionally contain customary propellants, such as, for example, chlorofluorohydrocarbons, volatile unsubstituted hydrocarbons, hydrocarbon ethers and compressed gases.

Transdermal patches have the added advantage of providing controlled delivery of the active (S)-trihexyphenidyl of the present invention to the body. Such dosage forms may be made by dissolving or dispersing the (S)-trihexyphenidyl in the proper medium. Absorption enhancers may also be used to increase the flux of the (S)-trihexyphenidyl across the skin. The rate of such flux can be controlled by either providing a rate controlling membrane or dispersing the (S)-trihexyphenidyl in a polymer matrix or gel.

Regardless of the route of administration selected, the pharmaceutical compositions of the present invention are formulated into pharmaceutically acceptable dosage forms by conventional methods known to those of skill in the art. Where necessary, the pharmaceutical compositions of the present invention are sterile or can be sterilized before administration to a patient.

In a preferred embodiment, the enantiomerically enriched trihexyphenidyl compositions of the present invention are provided in tablet or capsule form with, as inactive ingredients, dibasic calcium phosphate, lactose, magnesium stearate, providone and sodium starch glycolate. The capsules or tablets are preferably formulated with from about 0.25 mg to about 250 mg of (S)-trihexyphenidyl, more preferably with from about 0.50 mg to about 100 mg of (S)-trihexyphenidyl, and even more preferably with from about 1 mg to about 50 mg of (S)-trihexyphenidyl.

In another preferred embodiment, the enantiomerically enriched (S)-trihexyphenidyl preparations of the present invention are provided in soft elastic gelatin capsule form. The soft elastic gelatin capsules are preferably formulated with from about 0.25 mg to about 250 mg of (S)-trihexyphenidyl, more preferably with from about 0.50 mg to about 100 mg of (S)-trihexyphenidyl, and even more preferably with from about 1 mg to about 50 mg of (S)-trihexyphenidyl.

Actual dosage levels of (S)-trihexyphenidyl in the pharmaceutical compositions of the present invention may be varied so as to obtain an amount of the active ingredient which is effective to achieve the desired therapeutic response for a particular patient, composition, and mode of administration, without being toxic to the patient.

The selected dosage level and frequency of administration will depend upon a variety of factors including the route of administration, the time of administration, the rate of excretion of the particular compound being employed, the duration of the treatment, other drugs, compounds and/or materials used in combination with the (S)-trihexyphenidyl, the age, sex, weight, condition, general health and prior medical history of the patient being treated, and like factors well known in the medical arts. For example, the dosage regimen is likely to vary with pregnant women, nursing mothers and children relative to healthy adults.

A physician having ordinary skill in the art can readily determine and prescribe the effective amount of the pharmaceutical composition required. For example, the physician could start doses of the compound employed in the pharmaceutical composition of the present invention at levels lower than that required in order to achieve the desired therapeutic effect and gradually increase the dosage until the desired effect is achieved.

A suitable daily dose of (S)-trihexyphenidyl will be that amount of the compound which is the lowest dose effective to produce a therapeutic effect. Such an effective dose will generally depend upon the factors described above. Generally, the total daily dose of (S)-trihexyphenidyl for the conditions described herein may be from about 0.25 mg to about 500 mg, more preferably from about 0.50 mg to about 250 mg, and more preferably from about 1 mg to about 100 mg.

If desired, the effective daily dose of the active (S)-trihexyphenidyl may be administered as two, three, four, five, six or more sub-doses administered separately at appropriate intervals throughout the day, optionally, in unit dosage forms.

Another embodiment of the present invention relates to a kit for treating urinary incontinence, including, e.g., bladder detrusor muscle instability incontinence, stress incontinence, urge incontinence, overflow incontinence, enuresis, and post-prostectomy incontinence, wherein said kit comprises a pharmaceutical composition comprising enantiomerically enriched (S)-trihexyphenidyl, or a pharmaceutically acceptable salt thereof, and a pharmaceutically acceptable carrier, and instructions for administering enantiomerically enriched (S)-trihexyphenidyl for the treatment of urinary incontinence while reducing or eliminating anticholinergic adverse effects associated with racemic trihexyphenidyl or other incontinence drugs with anticholinergic action.

The utility of (S)-trihexyphenidyl may be established by the following studies of antimuscarinic, spasmolytic, and calcium entry blocking effects in models of receptor binding and bladder function.

Binding to Human $M_1$, $M_2$, $M_3$, $M_4$ and $M_5$ Muscarinic Receptor Subtypes These experiments are carried out on membranes prepared from SF9 cells infected with baculovirus to express the human recombinant $M_1$, $M_2$, $M_3$, $M_4$, and $M_5$ muscarinic receptor subtypes. The binding assays are performed as set forth in Table 1.

TABLE 1

| Receptor | Radioligand | Conc. | Nonspecific | Incubation time/temp. | Reference Compound |
|---|---|---|---|---|---|
| $M_{1H}$ | [$^3$H]piren$^{zepine}$ | 2 nM | atropine (1 μM) | 60 min/27° C. | pirenzepine |
| $M_{2H}$ | [$^3$H]AF-D$^{X\ 384}$ | 2 nM | atropine (1 μM) | 60 min/27° C. | methoctramine |
| $M_{3H}$ | [$^3$H]4-$^{DAMP}$ | 0.8 nM | atropine (1 μM) | 60 min/27° C. | 4-DAMP |
| $M_{4H}$ | [$^3$H]4-$^{DAMP}$ | 0.3 nM | atropine (1 μM) | 60 min/27° C. | 4-DAMP |
| $M_{5H}$ | [$^3$H]4-$^{DAMP}$ | 0.5 nM | atropine (1 μM) | 60 min/27° C. | 4-DAMP |

Following incubation, the assays are rapidly filtered under vacuum through GF/B glass fiber filters (available, e.g., from Whatman) and washed with an ice-cold buffer using a Brandel Cell Harvester. Bound radioactivity is determined with a liquid scintillation counter (e.g., LS 6000, Beckman) using a liquid scintillation cocktail (e.g., Formula 99, DuPont NEN).

The compounds are tested on each receptor at 10 concentrations in duplicate to obtain competition curves. In each experiment, the reference compound for the receptor under investigation is simultaneously tested at 8 concentrations in duplicate to obtain a competition curve in order to validate this experiment.

The specific radioligand binding of each receptor is defined as the difference between total binding and nonspecific binding determined in the presence of an excess of unlabelled ligand. $IC_{50}$ values (concentrations required to inhibit 50% of specific binding) are determined by non linear regression analysis of the competition curves. These parameters are obtained by curve fitting using Sigmaplot™ software.

Binding to Calcium Channels

Binding assays are performed using the methods set forth in Table 2.

TABLE 2

| Receptors | Membranes | Reference Compounds | References |
|---|---|---|---|
| Ca channel (T + L, diltiazem site) | rat cerebral cortex | diltiazem | Schoemaker and Langer (1985) |
| Ca channel (T + L, verapamil site) | rat cerebral cortex | D600 | Reynolds et al (1986) |

The experiment conditions are set forth in Table 3.

TABLE 3

| Receptors | Ligands | Concentrations | Nonspecific | Incubation |
|---|---|---|---|---|
| Ca channel (T + L, diltiazem site) | [$^3$H] diltiazem | 5 nM | dilitiazem (10 μM) | 120 min 25° C. |
| Ca channel (T + L, verapamil site) | [$^3$H]D $^{888}$ | 0.5 nM | D 600 (10 μM) | 60 min 22° C. |

Following incubation, the assays are rapidly filtered under vacuum through GF/B or GF/C glass fiber filters (available, e.g., from Whatman) and washed with an ice-cold buffer using a Brandel Cell Harvester. Bound radio-activity is determined with a liquid scintillation counter (e.g., LS 6000, Beckman) using a liquid scintillation cocktail (e.g., Formula 989, DuPont NEN).

The compounds are tested in duplicate on each receptor at a concentration of $10^{-5}$M. In each experiment, the reference compound for the receptor under investigation is simultaneously tested at 8 concentrations in duplicate to obtain a competition curve in order to validate this experiment.

The specific radioligand binding of each receptor is defined as the difference between total binding and nonspecific binding determined in the presence of an excess of unlabelled ligand. Mean values are expressed as a percentage of inhibition of specific binding. $IC_{50}$ values (concentration required to inhibit 50% of specific binding) are determined by non linear regression analysis of their competition curves. These parameters are obtained by curve fitting using Sigmaplot™ software.

Functional Characterization of Antimuscarinic/Antispasmodic Activity

The effects of (S)-trihexyphenidyl are studied in an in vitro model of bladder function. For example, isolated strips of guinea pig bladder smooth muscle are mounted in a tissue bath and contracted either with the muscarinic agonist carbachol or with increasing concentrations of external potassium.

Bladder strips. Experiments are performed using methods similar to those described by Kachur et al. (*J. Pharmacol. Exp. Ther.*, 247:867–872 (1988)) and Noronha-Blob and Kachur (*J. Pharmacol. Exp. Ther.*, 562–567 (1991)). Strips of tissue (approximately 10 mm long and 1.5 mm wide) are removed from the body of the urinary bladder of male guinea pigs weighing 400–600 g. (available, e.g., from Elm Hill Breeding Laboratories, Chelmsford, Mass.). The tissues are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7. The tissues are maintained at 37.5° C. Isometric contractions of the tissues are recorded by using appropriate transducers and an ink-writing polygraph. A resting tension of 0.5 grams is maintained on each tissue at all times.

Individual tissues are allowed to equilibrate with the bathing solution for one hour before proceeding with the experiment.

Carbachol-induced contractions. These series of experiments focus on anticholinergic actions. In these experiments, in order to assess the viability of each tissue and to serve as a frame of reference, the contractions of each strip of tissue are recorded initially in response to exposure to a tissue medium in which the NaCl is replaced by KCl to yield a concentration of 137.7 mM KCl in the medium. This is followed by return to the standard medium, and then by exposure to progressively increasing concentrations of carbachol, with separate exposure to each concentration only until the peak response has been recorded.

Then, leaving one strip untreated and/or one strip exposed to a vehicle to serve as control tissue(s), the remaining strips each are exposed for one hour to one concentration of an antagonist. The vehicle controls are used when, because of poor solubility, stock solutions of test substances are prepared in a vehicle, e.g., ethanol. Finally, the responses to increasing concentrations of carbachol followed by exposure to 137.7 mM KCl are recorded a second time.

Potassium-induced contractions. These experiments focus on the spasmolytic action of the substances being studied. Contractions are recorded in response to sequentially increasing the concentration of potassium in the medium.

To determine whether test substances decrease the peak response to agonists, the peak tension developed by each strip during the second set of determinations is expressed as a percent of the peak tension developed during the first concentration-effect determination. Then, for each test substance the resultant data are analyzed for treatment-related differences by one-way analysis of variance (ANOVA). Since only one concentration of test substance is studied in each strip of bladder, the procedures of Arunlakshana and Schild (1959) are used in modified form to estimate the pA2 and slope of the Schild regression.

First, the concentrations of agonist producing a half-maximal response (the $EC_{50}$) is estimated for each strip from the second set of concentration-effect data. The $EC_{50}$ is obtained from linear regression lines fit to the logarithm of the concentration of drug and the responses bracketing the half maximum level of response. For each drug-treated strip, a "concentration ratio" (CR) is calculated as the ratio of the $EC_{50}$ of the treated tissue divided by the $EC_{50}$ of the untreated tissue. For each experiment where two or more strips are exposed to the same test substance but at different concentrations, the logarithm of this ratio minus one [i.e., log (CR-1)] is plotted against the logarithm of the concentration of antagonist to which the strip had been exposed to produce "Schild plots". A regression analysis relating log (CR-1) to the logarithm of the concentration of the antagonist is employed to estimate the pA2 and the slope of the regression line.

Finally, experiments are grouped by test substance and the mean ±S.E. of the pA2 and slope are calculated. The 95% confidence limits (CL) for the slope are estimated from its S.E. using standard methods. For experiments in which only one strip is exposed to a given test substance, a pKD is calculated as (concentration of antagonist)/(CR-1) and the negative logarithm of the KD is then pooled with the pA2 values to yield an expanded set of pA2 values.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference.

Other embodiments are within the following claims.

What is claimed is:

1. A method for treating urinary incontinence, comprising administering to a subject in need thereof a therapeutically effective amount of enantiomerically enriched (S)-trihexyphenidyl, or a pharmaceutically acceptable salt thereof.

2. The method as recited in claim 1, wherein the enantiomerically enriched (S)-trihexyphenidyl, or a pharmaceutically acceptable salt thereof, is administered as a pharmaceutical composition comprising said enantiomerically enriched (S)-trihexyphenidyl, or a pharmaceutically acceptable salt thereof, and a pharmaceutically acceptable carrier.

3. The method as recited in claim 2, wherein said pharmaceutical composition is administered by oral, parenteral, transdermal, rectal, or vaginal administration.

4. The method as recited in claim 2, wherein said pharmaceutical composition is administered by injection.

5. The method as recited in claim 1, wherein a daily amount of (S)-trihexyphenidyl administered is about 0.25 mg to about 500 mg.

6. The method as recited in claim 5, wherein the daily amount of (S)-trihexyphenidyl administered is about 1 mg to about 100 mg.

7. The method as recited in claim 2, wherein (S)-trihexyphenidyl comprises greater than 50% by weight of the total trihexyphenidyl in said pharmaceutical composition.

8. The method as recited in claim 7, wherein (S)-trihexyphenidyl comprises at least 80% by weight of the total trihexyphenidyl in said pharmaceutical composition.

9. The method as recited in claim 1, wherein (S)-trihexyphenidyl is administered as a pharmaceutical composition comprising substantially enantiomerically enriched (S)-trihexyphenidyl, or a pharmaceutically acceptable salt thereof, and a pharmaceutically acceptable carrier.

10. The method as recited in claim 9, wherein (S)-trihexyphenidyl comprises at least 85% by weight of the total trihexyphenidyl in said pharmaceutical composition.

11. The method as recited in claim 10, wherein (S)-trihexyphenidyl comprises at least 99% by weight of the total trihexyphenidyl in said pharmaceutical composition.

12. The method as recited in claim 1, wherein the subject is treated for stress incontinence, urge incontinence, post-prostectomy incontinence, or enuresis.

13. A method for treating bladder detrusor muscle instability, said method comprising administering to a subject in need thereof a therapeutically effective amount of enantiomerically enriched (S)-trihexyphenidyl, or a pharmaceutically acceptable salt thereof.

14. The method as recited in claim 13, wherein said enantiomerically enriched (S)-trihexyphenidyl, or a pharmaceutically acceptable salt thereof, is substantially free of (R)-trihexyphenidyl.

15. A kit for treating urinary incontinence, wherein said kit comprises a pharmaceutical composition comprising enantiomerically enriched (S)-trihexyphenidyl, or a pharmaceutically acceptable salt thereof, and a pharmaceutically acceptable carrier, and instructions for administering enantiomerically enriched (S)-trihexyphenidyl for the treatment of urinary incontinence while reducing or eliminating concomitant liability of adverse effect.

16. The kit as recited in claim 15, wherein said adverse effect is one or more of drowsiness, epistaxis, xerostomia, mydriasis, cycloplegia, cardiovascular tachycardia, cardiovascular palpitations, increased ocular pressure, nausea, constipation, decreased sweating, impotence, or unwanted dermal manifestations.

17. A kit for treating urinary incontinence, wherein said kit comprises a pharmaceutical composition comprising substantially enantiomerically enriched (S)-trihexyphenidyl, or a pharmaceutically acceptable salt thereof, and a pharmaceutically acceptable carrier, and instructions for administering substantially enantiomerically enriched (S)-trihexyphenidyl for the treatment of urinary incontinence while reducing or eliminating concomitant liability of adverse effects.

18. The kit as recited in claim 17 wherein said adverse effect is one or more of drowsiness, epistaxis, xerostomia, mydriasis, cycloplegia, cardiovascular tachycardia, cardiovascular palpitations, increased ocular pressure, nausea, constipation, decreased sweating, impotence, or unwanted dermal manifestations.

* * * * *

UNITED STATES PATENT AND TRADEMARK OFFICE
CERTIFICATE OF CORRECTION

PATENT NO. : 6,063,792
DATED : May 16, 2000
INVENTOR(S) : Fabiano et al.

It is certified that error appears in the above-identified patent and that said Letters Patent is hereby corrected as shown below:

Claim 4, Col. 13, line 59, after "injection" insert -- or intravesical perfusion --.

Signed and Sealed this

Twenty-seventh Day of March, 2001

Attest:

NICHOLAS P. GODICI

Attesting Officer

Acting Director of the United States Patent and Trademark Office